United States Patent
Praly

(10) Patent No.: US 8,148,687 B1
(45) Date of Patent: Apr. 3, 2012

(54) SYSTEM AND METHOD FOR CREATING EQUIPMENT INSPECTION ROUTES

(75) Inventor: Sebastien Praly, Ben Lomond, CA (US)

(73) Assignee: Fluke Corporation, Everett, WA (US)

( * ) Notice: Subject to any disclaimer, the term of this patent is extended or adjusted under 35 U.S.C. 154(b) by 0 days.

(21) Appl. No.: 12/961,459

(22) Filed: Dec. 6, 2010

Related U.S. Application Data

(63) Continuation of application No. 11/463,234, filed on Aug. 8, 2006, now Pat. No. 7,847,251.

(51) Int. Cl.
 *G01J 5/00* (2006.01)
(52) U.S. Cl. ........................................ 250/330
(58) Field of Classification Search ................. 250/330
 See application file for complete search history.

(56) References Cited

U.S. PATENT DOCUMENTS

| | | |
|---|---|---|
| 5,637,871 A | 6/1997 | Piety et al. |
| 5,812,112 A | 9/1998 | Helfferich |
| 5,856,931 A | 1/1999 | McCasland |
| 6,594,621 B1 | 7/2003 | Meeker |
| 6,606,115 B1 | 8/2003 | Alicandro et al. |
| 7,561,200 B2 | 7/2009 | Garvey, III et al. |

OTHER PUBLICATIONS

Users Manual, "InsideIR: Thermal Image Analysis Software," Fluke Corporation, Jan. 2006.*
Users Manual, "Ti20: Thermal Imager," Fluke Corporation, Jan. 2006.*

* cited by examiner

*Primary Examiner* — Mark R Gaworecki
(74) *Attorney, Agent, or Firm* — Perkins Coie LLP

(57) ABSTRACT

A graphical user interface for creating and organizing equipment inspection routes is provided. The interface can be used to retrieve thermographic images from a portable infrared imager. Viewed as thumbnails, these images can be annotated and placed in a user-specified linear order defining an inspection route. The route information can be transferred to portable infrared imager and displayed on the imager as thermographic image data with annotations.

20 Claims, 8 Drawing Sheets

SYSTEM AND METHOD FOR CREATING EQUIPMENT INSPECTION ROUTES

CROSS REFERENCE TO RELATED APPLICATION

This application is a continuation of U.S. application Ser. No. 11/463,234, filed Aug. 8, 2006, now U.S. Pat. No. 7,847,251 titled "SYSTEM AND METHOD FOR CREATING EQUIPMENT INSPECTION ROUTES," the entirety of which application is incorporated herein by reference.

TECHNICAL FIELD

The following is related to equipment inspection devices and procedures, and more particularly, to systems and methods for defining equipment inspection routes using a graphical user interface.

BACKGROUND

Infrared thermal imaging instruments commonly are used for obtaining temperature profiles of objects such as industrial machines or components of operating equipment. Inspecting an object's operating temperature conditions can reveal whether a failure is imminent or a machinery adjustment is necessary. Portable imagers are particularly useful for inspecting a series of machines along a route in, for example, a factory.

Conventionally, a user of a portable imager would need to memorize and subsequently recall a series of locations at which certain components can be found for imaging. To improve the usability of an imager, an imager can be programmed to store a predefined route and prompt the user to proceed to the defined stops along the route.

Some known systems provide a base computer at which a user can define a route that subsequently can be transferred to a portable imaging system. Typically, however, such systems are unintuitive and difficult to use. Furthermore, while these systems may present the user with the name of the next component to be imaged, no other instruction or indication is provided to assist the user in successfully identifying the appropriate components along the route.

SUMMARY

A method, system, and machine-readable medium for creating equipment inspection routes are disclosed. In one embodiment, the method for defining an inspection route for use on a portable imaging device can include receiving data at a base computer from the portable imaging device, wherein the data corresponds to thermal images of objects, and wherein at least one of the objects is an inspection location, displaying a plurality of images corresponding to the downloaded data on the base computer, and receiving a user command to associate of at least one of the plurality of displayed images with an inspection route.

In another embodiment, the method for defining an inspection route for use on a portable imaging device can include generating a plurality of thermal images corresponding to one or more objects, and displaying a graphical user interface for receiving a user selection of a subset of the images to designate a route of locations to be inspected.

In another embodiment, the method for defining an inspection route for use on a portable imaging device can include receiving data from a thermal sensor, wherein the data corresponds to thermal emissions from an object at an inspection location, displaying on the portable imaging device a color image corresponding to the data, and receiving a user command to associate the color image with a route of locations to be inspected.

In another embodiment, the method for defining an inspection route for use on a portable imaging device can include generating a plurality of thermal images of objects and selecting a subset of those images to designate a route of locations to be inspected.

In another embodiment, a machine-readable medium having stored thereon instructions which, when executed by a processor, cause the processor to perform method for defining an inspection route for use on a portable imaging device, the method including receiving data at a base computer from the portable imaging device, wherein the data corresponds to thermal images of objects, and wherein at least one of the objects is an inspection location, displaying a plurality of images corresponding to the downloaded data on the base computer, and receiving a user command to associate of at least one of the plurality of displayed images with an inspection route.

In another embodiment, a portable imaging system for use on an inspection route can include a sensor for detecting infrared emissions and configured to generate thermal data corresponding to the detected emissions, a processor configured to receive the thermal data from the sensor and generate corresponding color data, a display in communication with the processor for displaying the color data as one or more thermographic images, and a user input device configured for receiving a user selection of a displayed thermographic image, wherein the processor is further configured to execute machine-readable instructions for designating the selected thermographic image as a route location to be inspected.

DETAILED DESCRIPTION

The computer graphical user interface described herein can be used to define one or more routes. A route, as the term is used herein, is a predefined set of physical locations to be inspected. The interface can be configured so that thermographic images captured using a portable imager can be annotated, organized, and later presented with the annotations to a user as a route to be followed when performing subsequent equipment inspections with a portable imager.

Figure 2:
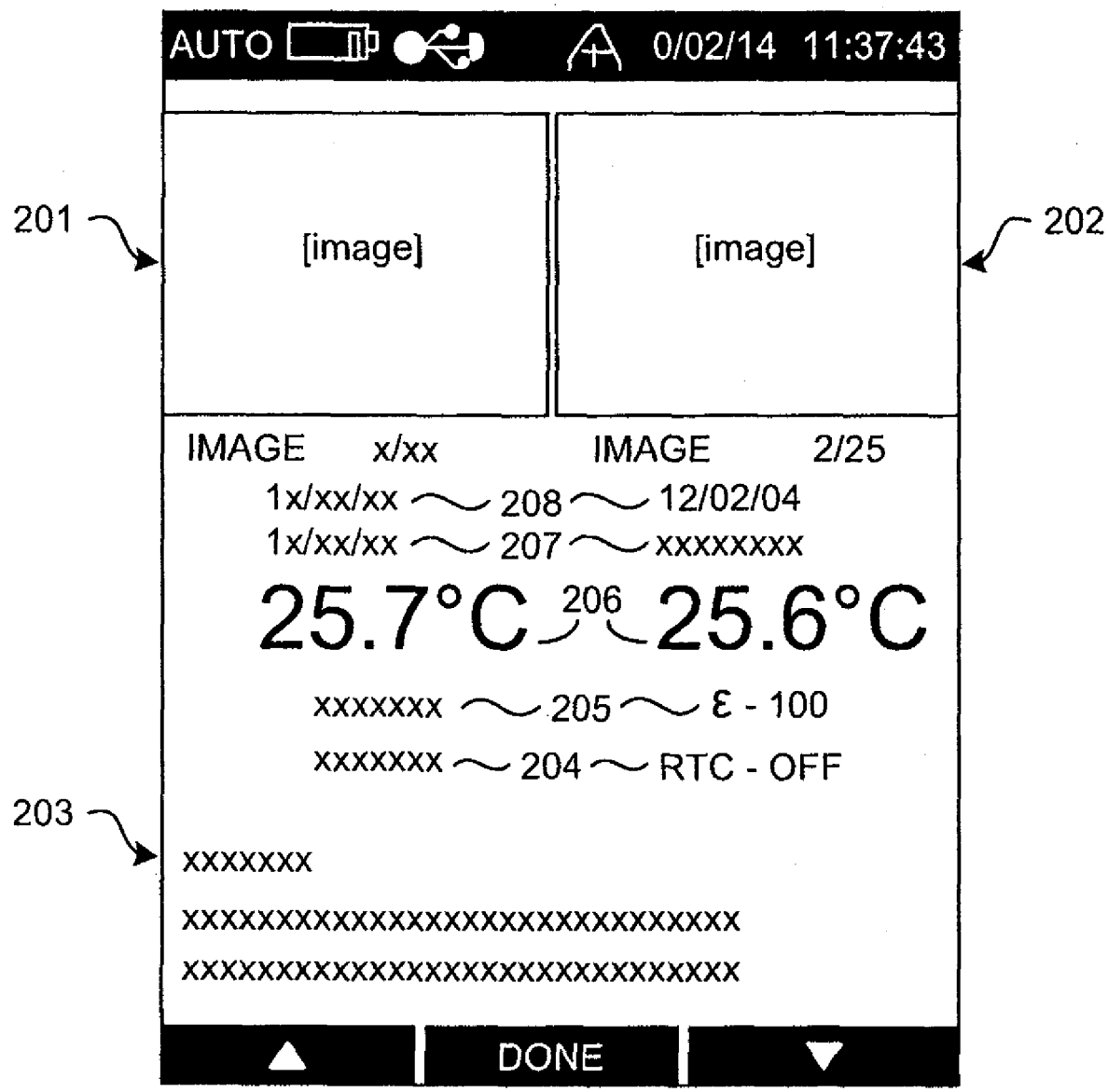
FIG. 2 illustrates an exemplary interface for displaying previously captured image data associated with a route.

FIG. 2 illustrates an exemplary display on a portable imager. Using this display, it will be easier for a user to follow a predefined route and obtain the desired thermographic data. The portable imager can be configured to display information corresponding to a previous inspection at a given location on a route as well as information corresponding to a current inspection at that location. As shown, a newly captured thermographic image can be displayed on the left portion of the screen (201) while a previously captured image is displayed on the right portion of the screen (202). This visual comparison of thermographic images can assist the user to confirm that the intended piece of equipment has been imaged from the intended vantage point. In addition to the dual display of images, other data associated with a route location also can be displayed. Additional data can include, as non-limiting examples, location information (203), temperature compensation factors (204), emmissivity (205), target temperature (206), time (207) and date (208). This data associated with a previously stored image can be provided by a user through a base computer and transferred to the imager using systems and methods described in more detail below.

The computer graphical user interface described in more detail below can be used to create and modify route information for use on a portable imager. It can be implemented on a base computer such as a laptop or desktop computer, implemented entirely on the portable device, or on a combination of the portable device and base computer. While the description below is made with reference to thermographic images, one of ordinary skill in the art would recognize that the systems and methods described could be applied to any type of image data.

Collections Interface

In at least one embodiment, a first step in creating a graphical route is for a user to capture one or more thermographic images on a portable imaging device. Once a user has captured a series of images on a portable device, the images can be downloaded or otherwise transferred to a host computer. This transfer can be performed via a USB, Firewire, serial, parallel, or other wired or wireless conduit.

Figure 3:
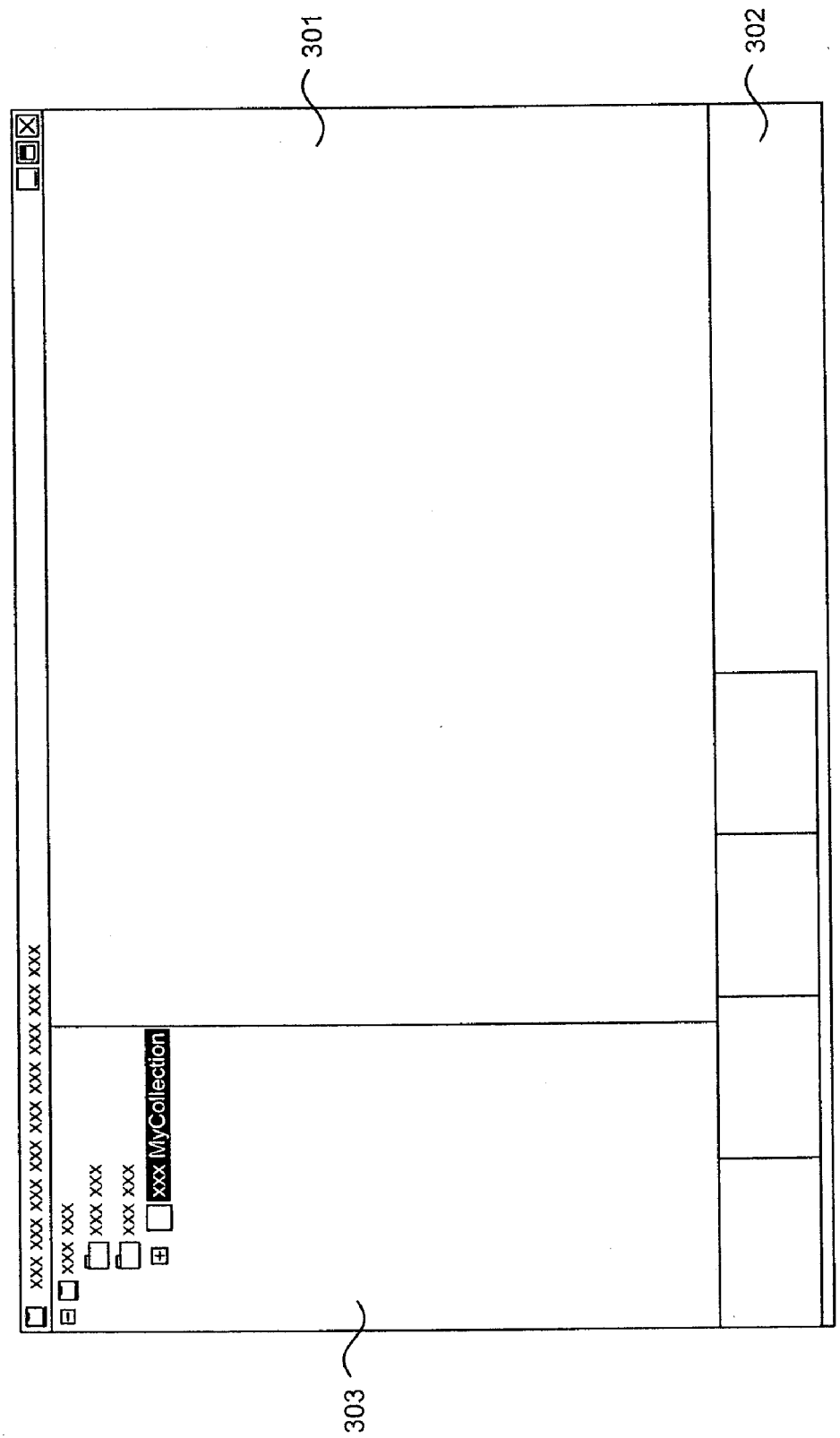
FIG. 3 illustrates an exemplary interface for displaying and managing collections of images and routing thumbnails.
Figure 4:
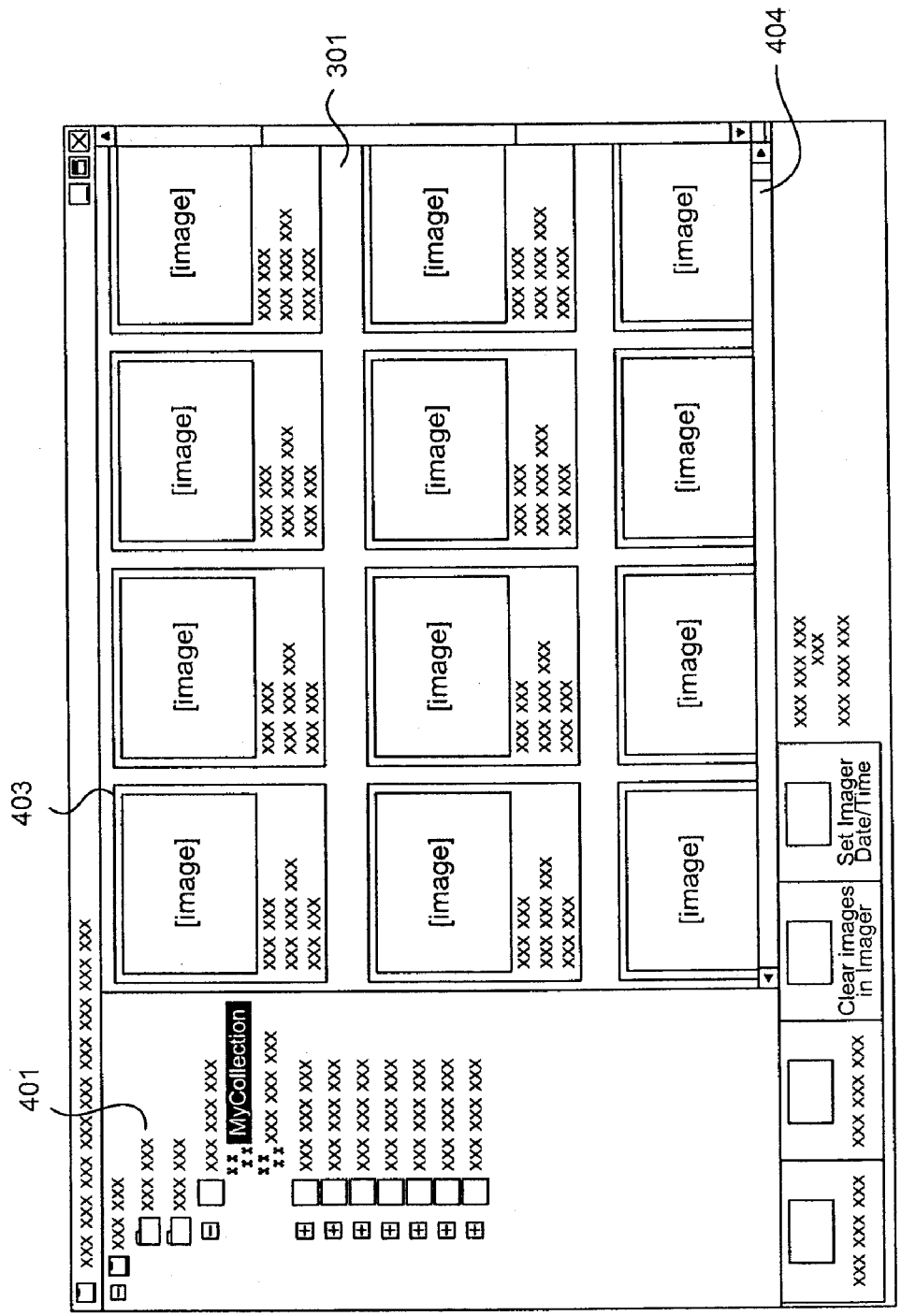
FIG. 4 illustrates an exemplary populated interface for displaying and managing routing thumbnails.

FIG. 3 illustrates an exemplary basic window configuration for managing downloaded images. As shown in FIG. 3, the basic window configuration can include a pane area (301) for displaying thumbnails of the images. A button area (302) can be provided for displaying functional buttons or icons. A folder view area (303) can be provided for displaying a tree view of folders for storing one or more hierarchical collections of images. FIG. 4 illustrates a populated view of the same interface. As shown in FIG. 4, the pane area (301) can be configured to display a plurality of thumbnails corresponding to images taken at inspection locations.

Once a thermographic image has been transferred to the host computer, additional analysis can be performed. For example, the interface can be configured to display the temperature of any target point on a thermographic image. A target temperature point can be user-selected using any suitable interface device.

Background Discussion of Thumbnails

Thumbnails representing larger thermographic images are useful in a GUI as they enable the interface to display several smaller images simultaneously when several full size images could not all simultaneously fit on a single screen of the display. In some embodiments, to navigate within the GUI, such as to select a particular thumbnail to be opened or viewed, a screen cursor or pointer can be used. The cursor or pointer can be displayed as a small arrow which, in combination with a mouse click, allows the user to select a displayed object such as a thumbnail. The screen cursor can be moved to a desired screen location in response to movements of a pointing device (e.g., a mouse, trackball, or similar device) by the user. The pointing device can include one or more switches or buttons for receiving additional user input.

As used herein, a "thumbnail" is a quantity of data which is derived from a larger quantity of data, such as an image file. To obtain a thumbnail, an image file can be opened and optically reduced or scaled to a smaller size; or, alternately, discrete portions of data from the file can be copied from the file. Thumbnail data, as used herein, can include a quantity of data which may be stored in any suitable form, for example ASCII or binary formats.

In some embodiments, a thumbnail is an image whose size has been reduced to decrease the amount of display space required to render the thumbnail image. In general, the thumbnails described herein need only be sufficiently detailed to provide a viewer sufficient visual information concerning the content of the original image, such as to enable the viewer to decide whether to view the corresponding original image or to enable to viewer to recognize the subject of the image. The actual size of thumbnail images can vary depending on a variety of factors, some of which may be defined by a user. In some embodiments, the thumbnail displayed can incorporate the full resolution of the original acquired image.

In some embodiments, the interface can be configured to display data associated with thumbnails. The display data can include, but is not limited to, metadata and other data including location data, caption data, and descriptive text.

Image data received from a portable imager can be stored and managed as a collection of images and displayed as thumbnails in the collections interface. The GUI arrangement illustrated in FIG. 3 can provide a hierarchy of containers into which individual images can be organized and can be used for accessing and managing thumbnails. When a folder is opened in the context of the GUI, a set of icons or thumbnails can be displayed, each icon or thumbnail being associated with one image or route location in the folder. For example, a set of thumbnails can be placed in a folder which can, in turn, be placed in another folder, and so forth, up to any level in the hierarchy.

Organizing Collections

Images downloaded from the imager can be organized using a graphical user interface. This interface on the host computer can be used to organize images downloaded from a portable imager in one or more collections. In some embodiments, the images can be stored in sets so that some or all of images collected along each route are stored in a single collection. The interface can be configured to enable any operation on the collected images, either individually or in groups. Exemplary operations include, but are not limited to, renaming, deleting, copying, and moving thumbnails of the images.

In some embodiments, after downloading image data from the portable device, the interface can open the Collections folder (401) automatically. The Collections folder (401) can be configured to be the default folder location for all new collections downloaded from the imager. At any later time, an image from any collection can be moved to an alternate collection or folder using any user input device.

Figure 5:
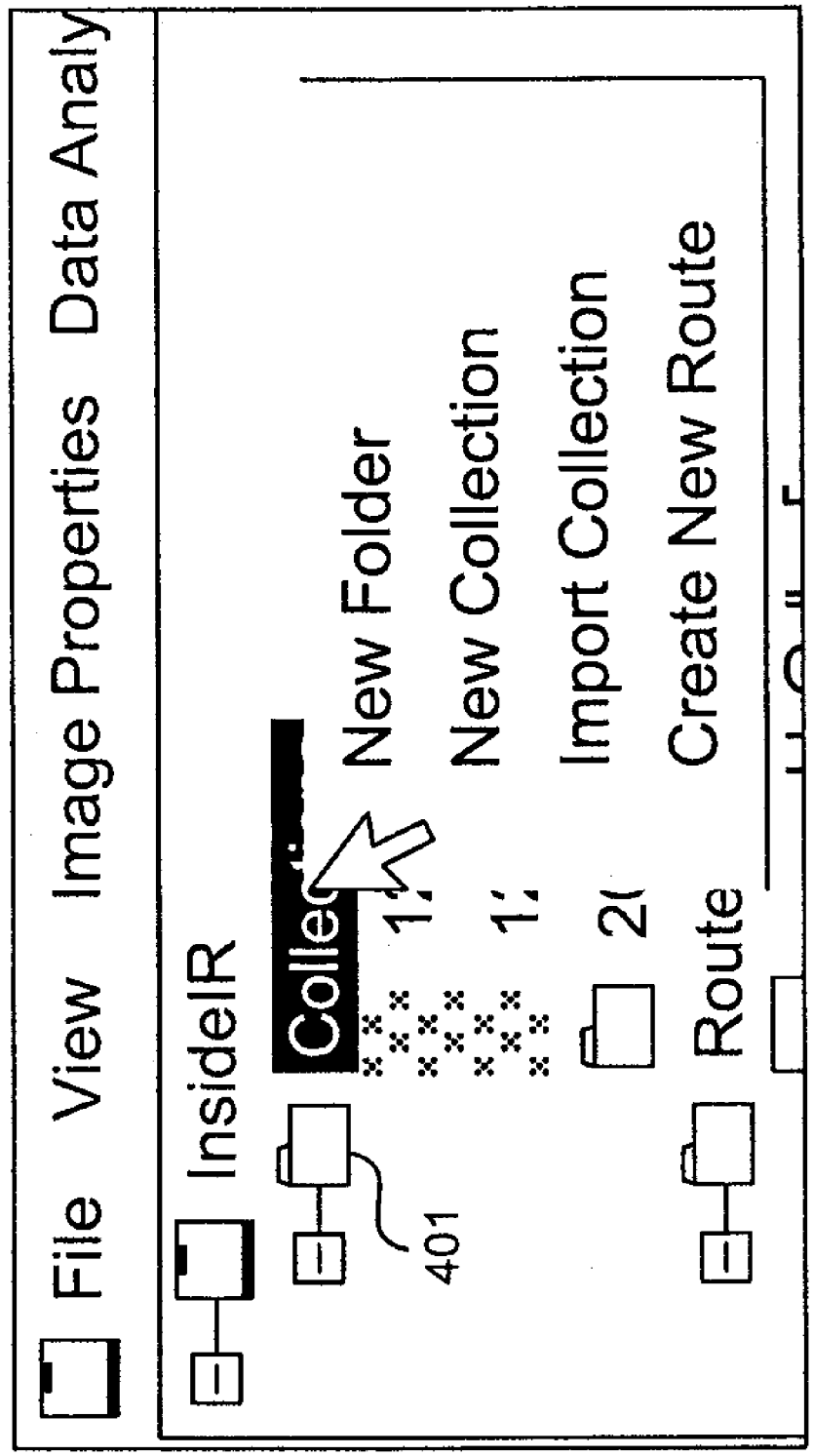
FIG. 5 illustrates an exemplary menu for managing a folder containing one or more collections of images.

The interface can be configured so that a user can "right-click" on the top level Collections folder (401) to perform a variety of functions. Exemplary functions are illustrated in FIG. 5. These functions can include, for example, New Folder, New Collection, and Import Collection. The New Folder command can be configured to create a new folder into which newly acquired or existing images can be placed. The new folder can, by default, be named based on the date and time it was created. The New Collection command can be configured to create a new collection in the top-level collection folder. The new collection can, by default, be named based on the date and time it was created. The Import Collection command can be configured to import a collection of images in a compressed or uncompressed eXtensible Markup Language (XML) format including collection and imager details.

Route Definition

Once one or more thermographic images have been collected, an inspection route can be defined.

In some embodiments, simple placement of an image thumbnail in a route folder is sufficient to define a route. In other embodiments, one or more other user actions can be performed for the purpose of designating an image as a part of a route.

A route can be defined in any one of various ways including by designating one or more images already stored or organized in a folder, as described above. As illustrated in FIG. 5, the interface can be configured so that a user can employ a mouse or other input device to right-click or otherwise select the top level Collections folder (401) to invoke a Create New Route command. The Create New Route command can be configured to create a new route in the top-level route folder. The route name need not be specified at the time of creation and can initially be empty.

Figure 6:
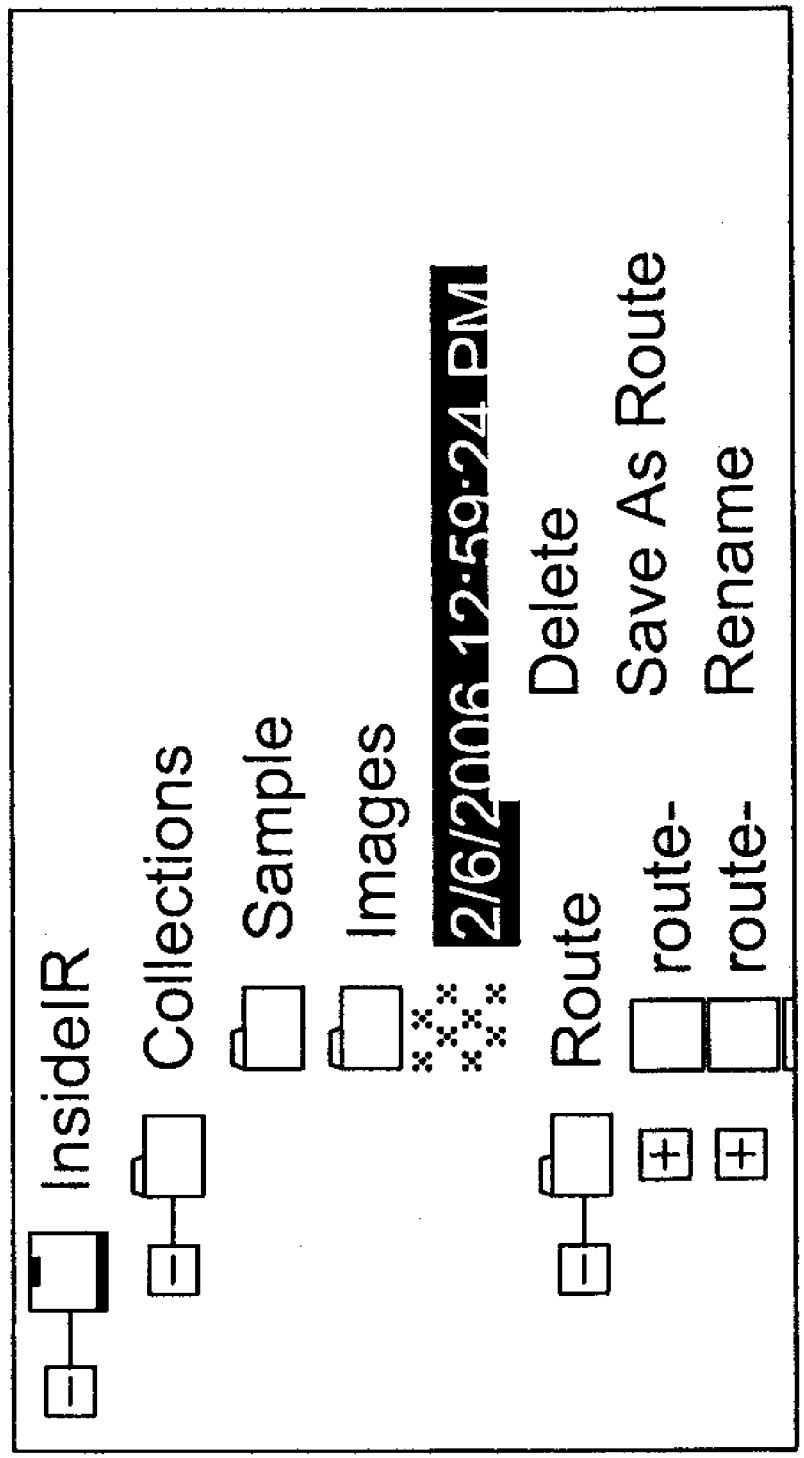
FIG. 6 illustrates an exemplary menu for managing a collection of images.

Additionally, an entire collection of images can be saved as a route using the interface shown in FIG. 6. The interface can be configured so that invoking the "Save As Route" command causes the selected collection of images to be saved in the Routes folder as a route.

Figure 7:
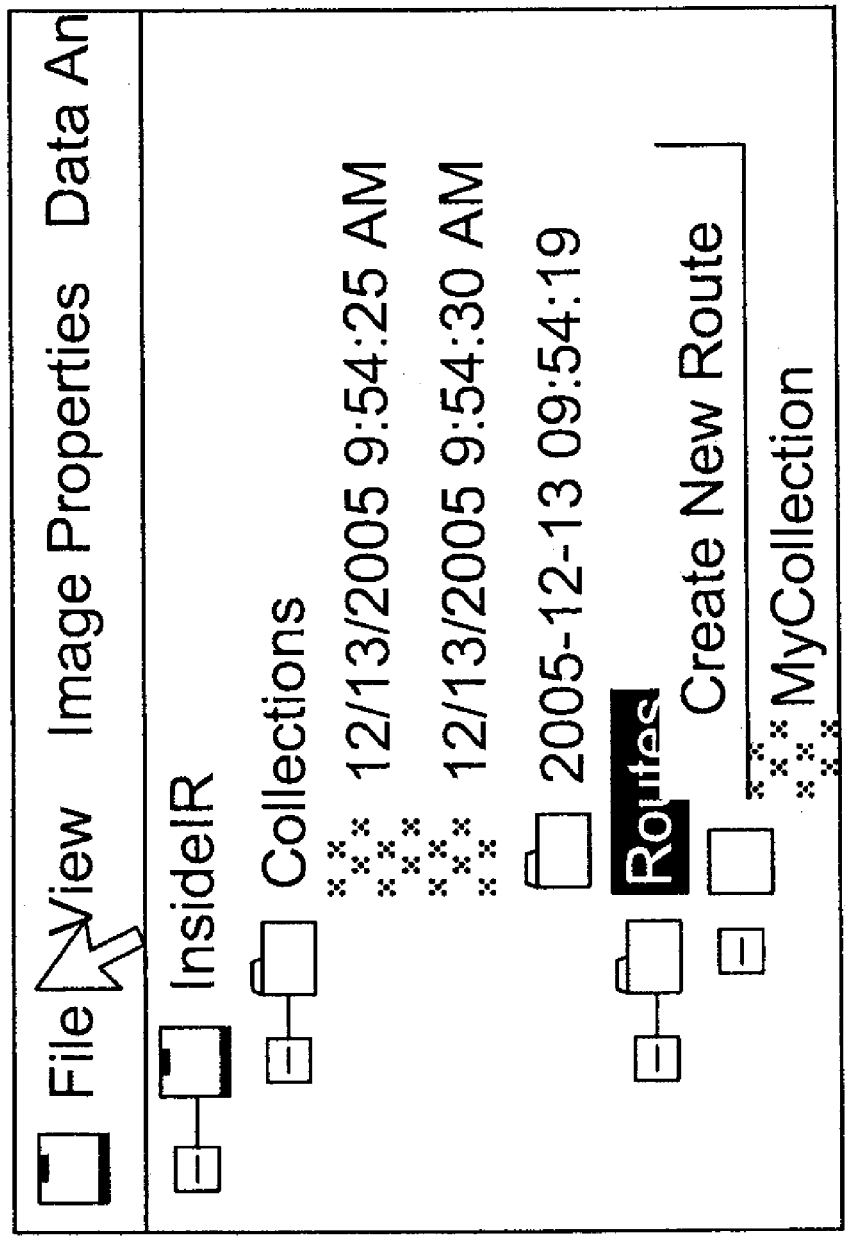
FIG. 7 illustrates an exemplary menu for managing a folder containing one or more collections of routing thumbnails.

FIG. 7 illustrates a pop-up menu interface for creating a new route. Through this interface, a user can right-click on the top level route menu to perform a variety of functions. For example, the interface can provide a Create New Route function to create a new route in the top-level routes folder. If a route name is not specified, the new folder can show the date and time it was created. If a user a right-clicks on a route, a command to Delete or Copy that route can also be presented.

Organizing Routes

With reference to FIG. 4, the order of the images in pane area (301) determines the relative order of locations in an inspection route. Given that an individual using one portable imager to inspect components along a route can inspect only one component at a time, the thumbnails can be arranged so that the displayed sequence corresponds to an intended route. For example, the images may be read from left to right in a horizontal array. In one embodiment, an image at the top (403) of the list in pane area (301) can correspond to the first location on a route, while an image at the bottom (404) of the pane area (301) can correspond to the last location on the route.

The interface illustrated in FIG. 4 includes a series of images defining a route. These images may be numbered sequentially and displayed in various arrangements. In the exemplary embodiment illustrated in FIG. 4, the route thumbnails are arranged in rows and columns. Other arrangements are possible. As discussed in more detail below, a user can define and modify a route by rearranging, adding, and deleting thumbnails in the route view. In some embodiments, an interface on a base computer can be provided so that the user can enter identifying information for the images to be included in the route as a particular object, machine component, device, or location. This information can be associated with image thumbnails and transferred with the thumbnails should the thumbnails or their associated images be transferred, copied, or exported to another location on the base computer or on the portable imager.

Figure 8:
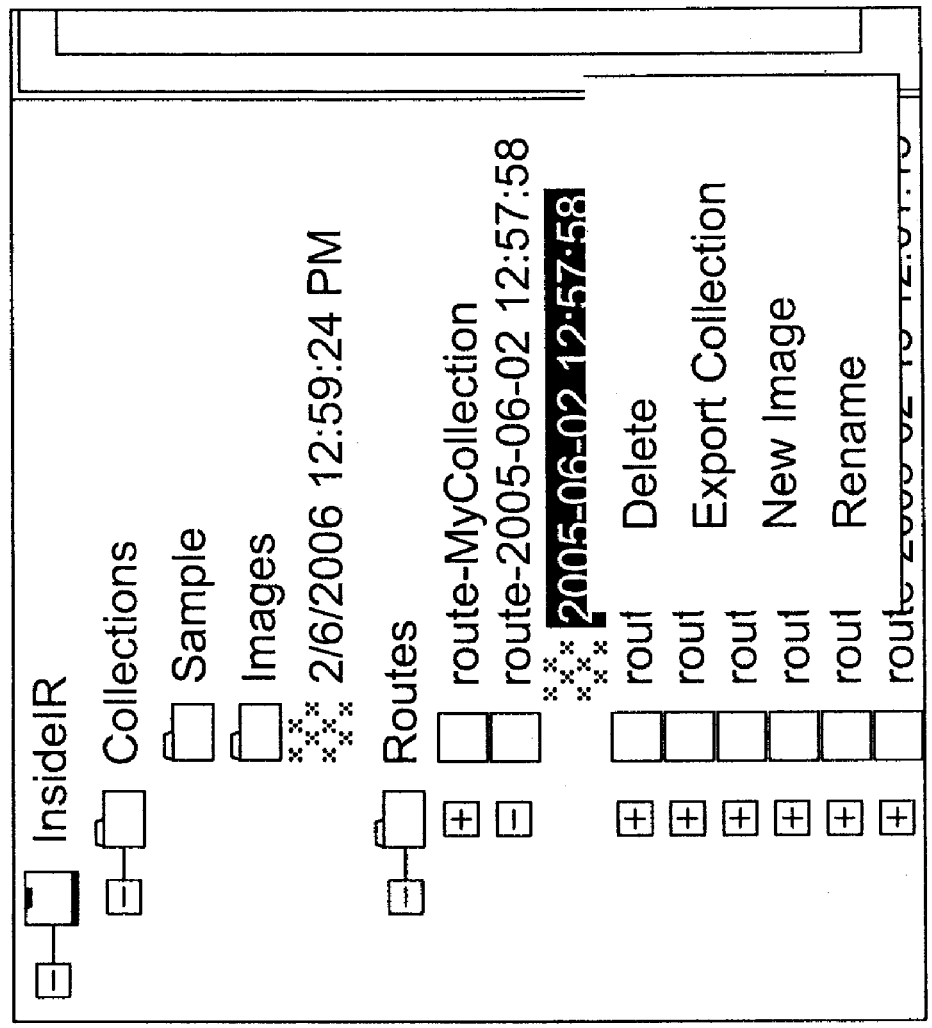
FIG. 8 illustrates an exemplary menu for managing a collection of routing thumbnails.

FIG. 8 illustrates additional functions that can be performed on a route. The Delete function can be configured to delete the collection within the route. The Export Collection function can be configured to export the route as a collection to another folder. The New Image function can be configured to create a blank image as a place holder for a route location and a user can then edit the attributes of the image to be taken. The Rename function can be configured to rename the route.

Once a route has been defined, it can be downloaded to a portable imager using any suitable communication channel known to one of ordinary skill in the art. The routing thumbnails or other graphical indicia can then be displayed on the portable imager to suggest the predefined inspection route to a user.

Embodiments of Methods for Arranging Routing Thumbnails

As discussed above, a route is a linear series of locations to be inspected. As such, in some embodiments, the displayed order of routing thumbnails specifies the order of components to be inspected. Some embodiments can provide an interface for rearranging the thumbnails to thereby reorder the specified route.

With reference to FIG. 3, a pane area (301) provides an interface for a user to select one or more routing thumbnails from a currently selected collection of thumbnails and/or routes. On first use, the routing thumbnails list can be populated with the routing thumbnails from a predetermined folder. When the selected folder is empty, the pane area (301) will be empty until a user selects a different folder.

The interface can be configured so that routing thumbnails will appear in the pane area (301) in the order in which they are acquired with a portable imager. The interface can be configured so that the pane area (301) is scrollable. A user can use the interface to select multiple routing thumbnails from among those displayed in pane area (301). "Shift-select" can be used to select a range of routing thumbnails, and "Ctrl-select" can be used to select multiple discontinuous routing thumbnails.

Images can be removed from the pane area (301) by selecting one or more images and actuating a remove control. While not separately shown, if a user desires to manipulate or edit (adding, removing, or relocating) routing thumbnails in an existing pane, a menu or other mechanism can be made available to present these features. Single or multiple routing thumbnails that appear in sequence can be selected and reorganized or reordered.

For example, the user may select three adjacent thumbnails that currently appear in the middle of the pane (301). After selecting those three thumbnails, a user can actuate a mouse or other human interface device to move those images to another location on the pane (301). In other embodiments, up, down, left or right controls can be employed to change the order of thumbnail images in the pane (301). The interface can be further configured to permit a user to arrange routing thumbnails by clicking on and dragging one or more thumbnails in one collection or route and dropping them at a selected position in another route or at a selected position in the same route.

Thumbnails can be moved between routes by clicking on the thumbnail in order to select the thumbnail and then dragging the thumbnail onto another folder displayed in folder view area (303) while pressing a mouse button down. When the mouse button is released while the thumbnail is above the folder, the thumbnail is copied from the first folder into the selected folder.

Suitable Systems

Figure 1:
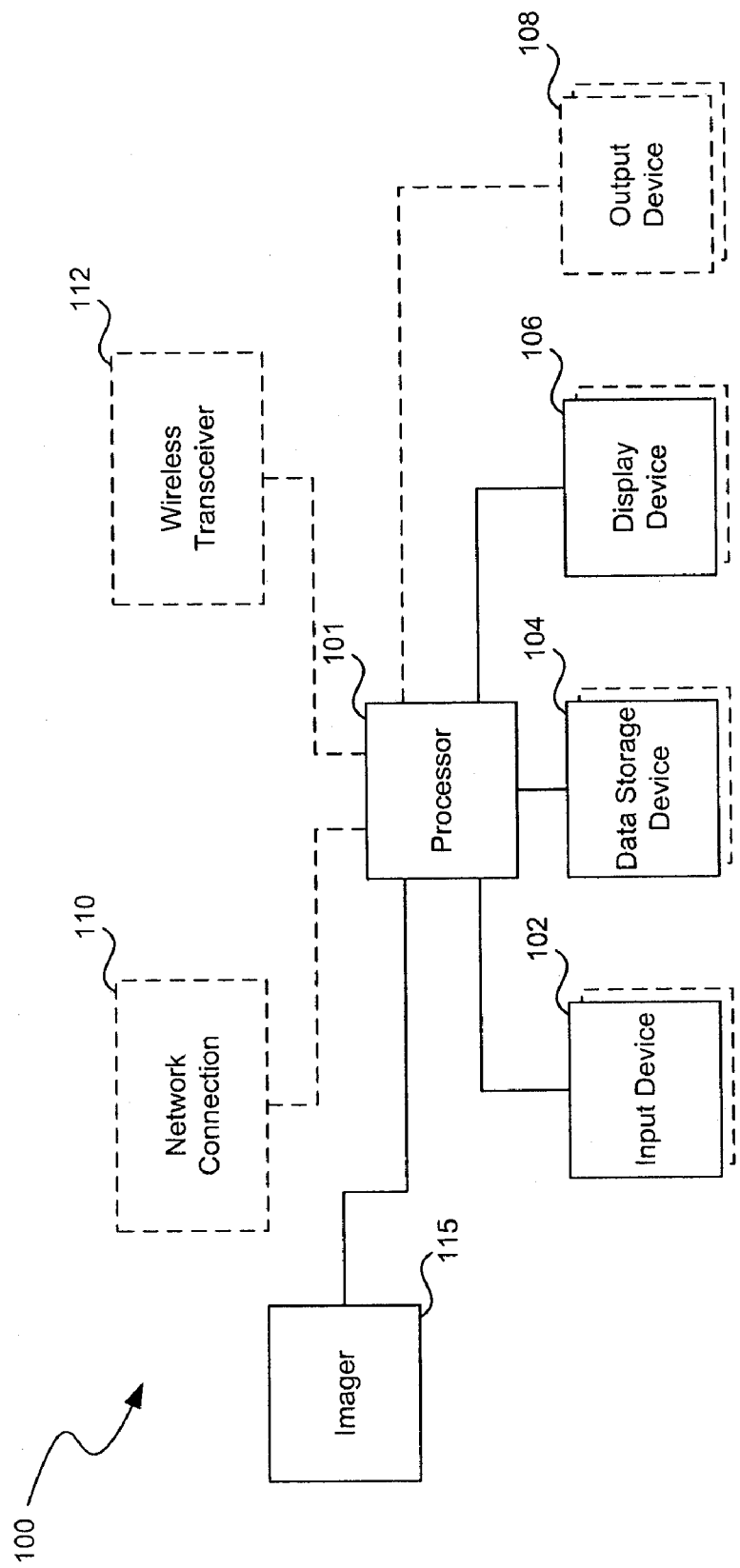
FIG. 1 illustrates an exemplary suitable computer for practicing the disclosed interface.

FIG. 1 and the following discussion provide a brief, general description of a suitable computing environment in which various embodiments of the disclosed interface can be implemented. Although not required, aspects and embodiments will be described in the general context of computer-executable instructions, such as routines executed by a general-purpose computer, e.g., a server or personal computer. Those skilled in the relevant art will appreciate that the embodiments can be practiced with other computer system configurations, including Internet appliances, hand-held devices, wearable computers, cellular or mobile phones, multi-processor systems, microprocessor-based or programmable consumer electronics, set-top boxes, network PCs, mini-computers, mainframe computers and the like. The embodiments can be embodied in a special purpose computer or data processor that is specifically programmed, configured or constructed to perform one or more of the computer-executable instructions explained in detail below. The term "computer", as used generally herein, refers to any of the above devices, as well as any data processor.

The embodiments can also be practiced in distributed computing environments, where tasks or modules are performed by remote processing devices, which are linked through a communications network, such as a Local Area Network ("LAN"), Wide Area Network ("WAN") or the Internet. In a distributed computing environment, program modules or sub-routines may be located in both local and remote memory storage devices. Aspects of the interface described below may be stored or distributed on computer-readable media, including magnetic and optically readable and removable computer discs, stored as firmware in chips (e.g., EEPROM chips), as well as distributed electronically over the Internet or over other networks (including wireless networks). Those skilled in the relevant art will recognize that portions of the interface may reside on a server computer, while corresponding portions reside on a client computer. Data structures and transmission of data particular to aspects of the interface are also encompassed within the scope of the disclosure.

Referring to FIG. 1, one embodiment of the interface employs a base computer (100), such as a personal computer or workstation, having one or more processors (301) coupled to one or more user input devices (102) and data storage devices (104). The computer is also coupled to at least one output device such as a display device (106) and one or more optional additional output devices (108) (e.g., printer, plotter, speakers, tactile or olfactory output devices, etc.). The computer may be coupled to external computers, such as via an optional network connection (110), a wireless transceiver (112), or both. The base computer (100) can be in electronic communication with a portable imager (115) so that data can be transferred between the base computer (100) and imager (115). The transfer of data can be performed via a USB, Firewire, serial, parallel, or other wired or wireless conduit.

The input devices (102) may include a keyboard and/or a pointing device such as a mouse. Other input devices are possible such as a microphone, joystick, pen, game pad, scanner, digital camera, video camera, and the like. The data storage devices (104) may include any type of computer-readable media that can store data accessible by the computer (100), such as magnetic hard and floppy disk drives, optical disk drives, magnetic cassettes, tape drives, flash memory cards, digital video disks (DVDs), RAMs, ROMs, smart cards, etc. Indeed, any medium for storing or transmitting computer-readable instructions and data may be employed, including a connection port to or node on a network such as a local area network (LAN), wide area network (WAN) or the Internet (not shown in FIG. 1).

Aspects of the interface may be practiced in a variety of other computing environments. User computers may include other program modules such as an operating system, one or more application programs (e.g., word processing or spread sheet applications), and the like. The computers may be general-purpose devices that can be programmed to run various types of applications, or they may be single-purpose devices optimized or limited to a particular function or class of functions. Any application program for providing a graphical user interface to a user may be employed.

Many specific details of certain embodiments of the invention are set forth in the description and in FIGS. 1-8 to provide a thorough understanding of these embodiments. A person skilled in the art, however, will understand that the invention may be practiced without several of these details or additional details can be added to the invention. Well-known structures and functions have not been shown or described in detail to avoid unnecessarily obscuring the description of the embodiments of the invention.

From the foregoing, it will be appreciated that specific embodiments of the invention have been described herein for purposes of illustration, but that various modifications may be made without deviating from the invention. Aspects of the invention described in the context of particular embodiments may be combined or eliminated in other embodiments. Further, while advantages associated with certain embodiments of the invention have been described in the context of those embodiments, other embodiments may also exhibit such advantages, and not all embodiments need necessarily exhibit such advantages to fall within the scope of the invention.

I claim:

1. In a base computer, a method for defining an inspection route, comprising:

causing to be displayed a plurality of thermal images wherein at least a subset of the thermal images are of locations associated with a route; and receiving user input for organizing a first subset of the thermal images from the displayed plurality of thermal images to define a first route of inspection locations; and transferring the organized first subset of the thermal images defining the first route of inspection locations to a portable imaging device.

2. The method of claim 1, further comprising:

receiving one or more annotations associated with one or more of the thermal images; and transferring the one or more annotations associated with the first subset of the thermal images to the portable imaging device.

3. The method of claim 1, further comprising:

receiving a user selected target location on at least one of the thermal images in the first subset of the thermal images; and analyzing the at least one of the thermal images to determine a temperature at the target location; and transferring the temperature at the target location along with the first subset of the thermal images to the portable imaging device.

4. The method of claim 1, further comprising:

receiving user input for organizing a second subset of the thermal images to define a second route of inspection locations; and transferring the organized second subset of the thermal images defining the second route of inspection locations to the portable imaging device from the base computer.

5. The method of claim 1 wherein the user input comprises specification of at least one ordering of the thermal images defining the first route of inspection locations.

6. The method of claim 1, wherein a first transferred thermal image from the first subset is displayed on the portable imaging device in proximity to a new thermal image generated during a new inspection, and wherein the first transferred thermal image and the new thermal image correspond to a same location.

7. The method of claim 6, further comprising:
transferring data associated with route locations to a portable imaging device;
collecting data associated with thermal images generated during the new inspection; and
displaying on the portable imaging device data associated with the first thermal image in proximity to data associated with the new thermal image.

8. A method for defining an inspection route for use on a portable imaging device, comprising:
generating a plurality of thermal images corresponding to one or more objects;
displaying the plurality of thermal images via a graphical user interface, and
receiving user input through the graphical user interface for arranging at least a subset of the plurality of thermal images to define a route of locations to be inspected.

9. The method of claim 8 wherein the user input comprises specification of at least one ordered arrangement of the subset of the thermal images displayed on the graphical user interface, an addition of thermal images to the sequential arrangement of the subset of the thermal images displayed via the graphical user interface, and a deletion of thermal images from the sequential arrangement of the subset of the thermal images displayed via the graphical user interface.

10. The method of claim 8, further comprising:
receiving annotations for at least one of the plurality of thermal images; and
displaying the annotations with the corresponding thermal images via the graphical user interface.

11. The method of claim 8, further comprising:
receiving the subset of the plurality of thermal images defining the route of locations to be inspected at a base computer from the portable imaging device; and
transferring subset of the plurality of thermal images defining the route of locations to be inspected to a second portable imaging device from the base computer.

12. The method of claim 8, further comprising:
receiving a user selected target location on at least one of the thermal images; and
analyzing the at least one of the thermal images to determine a temperature at the target location.

13. A method for defining an inspection route for use on a portable imaging device, comprising:
generating a plurality of thermal images of objects;
displaying at least some of the plurality of thermal images on a display; and
receiving a user selection of a first subset of the thermal images in a specified order to define a first route of locations to be inspected.

14. The method of claim 13, further comprising displaying on the portable imaging device one of the first subset of the thermal images of a first object and at least one other thermal image previously acquired of the first object.

15. The method of claim 13, further comprising receiving a user selection of a second subset of the thermal images on the display that define a second route of locations to be inspected, wherein the second subset includes at least one image from the first subset associated with the first route of locations to be inspected.

16. The method of claim 13, further comprising receiving and displaying one or more annotations associated with one or more of the displayed images.

17. The method of claim 13, further comprising:
receiving a modification of the sequential order of one or more of the images on the display.

18. The method of claim 17 wherein the modification of the sequential order comprises a selection of one or more of the images and an indication of repositioning of the selected images relative to images not selected.

19. An apparatus, comprising:
means for displaying a plurality of images on a base computer, wherein at least a subset of the thermal images are of locations to be inspected in a route; and
means for receiving user input for organizing a first subset of the displayed thermal images to define a first route of inspection locations;
means for ordering the first subset of the displayed thermal images responsive to the user input; and
means for transferring the organized first subset of the thermal images defining the first route of inspection locations to a portable imaging device from the base computer.

20. An apparatus, comprising:
means for generating a plurality of thermal images of objects;
means for displaying at least some of the plurality of thermal images on a display; and
means for receiving a user selection of a first subset of the thermal images in a sequential order of the first subset of the thermal images that define a first route of locations to be inspected.

* * * * *